US00PP17664P2

(12) United States Plant Patent
Fraser

(10) Patent No.: US PP17,664 P2
(45) Date of Patent: Apr. 24, 2007

(54) ***HEBE* PLANT NAMED 'TURKISH DELIGHT'**

(50) Latin Name: *Hebe mathewsii*
Varietal Denomination: Turkish Delight

(76) Inventor: Peter Fraser, P.O. Box 29, Kihikihi Waikato (NZ)

( * ) Notice: Subject to any disclaimer, the term of this patent is extended or adjusted under 35 U.S.C. 154(b) by 10 days.

(21) Appl. No.: 11/254,484

(22) Filed: Oct. 20, 2005

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent Bell

(57) ABSTRACT

A new cultivar of *Hebe* plant named 'Turkish Delight' that is characterized by burgundy colored leaves, a compact growth habit and free branching.

1 Drawing Sheet

Botanical classification: *Hebe mathewsii*.
Variety denomination: 'Turkish Delight'.

BACKGROUND OF THE INVENTION

The present invention relates to a new and distinct cultivar of *Hebe* plant botanically known as *Hebe mathewsii* and hereinafter referred to by the cultivar name 'Turkish Delight'.

'Turkish Delight' is a naturally occurring branch mutation of *Hebe* 'Mrs. Winder' (not patented). The cultivar 'Turkish Delight' was discovered by the inventor in April of 2002 in a cultivated area of Kihikihi, Wakato, New Zealand.

Asexual reproduction of the new cultivar 'Turkish Delight' by terminal cuttings was first performed in March of 2003 in Kihikihi, Wakato, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Hebe* cultivar 'Turkish Delight'. These traits in combination distinguish 'Turkish Delight' as a new and distinct cultivar.

1. *Hebe* 'Turkish Delight' exhibits burgundy colored leaves.
2. *Hebe* 'Turkish Delight' exhibits a compact growth habit.
3. *Hebe* 'Turkish Delight' exhibits free branching.

The new cultivar 'Turkish Delight' is distinguishable from the parent *Hebe* 'Mrs. Winder' by the following characteristics:

1. 'Turkish Delight' has burgundy leaves. The young leaves of 'Mrs. Winder' are green.
2. 'Turkish Delight' has a leaf length of 35 mm. The leaves of 'Mrs. Winder' are 25 mm is length.
3. 'Turkish Delight' has a mature leaf width of approximately 10 mm. The leaves of 'Mrs. Winder' have mature leaf width of approximately 6 mm.

The closest comparison cultivar is the parent plant *Hebe* 'Mrs. Winder'.

BRIEF DESCRIPTION OF THE DRAWING

The accompanying photograph illustrates the distinguishing traits of *Hebe* 'Turkish Delight'. The plant in the photograph shows an overall view of an 18 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Hebe* cultivar named 'Turkish Delight'. Data was collected in Kihikihi, Wakato, New Zealand from 18 month old outdoor grown plants in 6 Liter containers. The time of year was Winter and the daytime temperature ranged from 5–15° Centigrade. The nighttime temperature ranged from 1–8° Centigrade. The light level was natural outdoor light and there were no photoperiodic treatments. Color determinations are in accordance with The Royal Horticultural Society Colour Chart 2001 edition, except where general color terms of ordinary dictionary significance are used. The growing requirements are similar to the species. 'Turkish Delight' has not been tested under all possible conditions and phenotypic differences may be observed with variations in environmental, climatic, and cultural conditions, however, without any variance in genotype.

Botanical classification: *Hebe* 'Turkish Delight'.
Use: Evergreen Shrub.
Parentage: 'Turkish Delight' is a naturally occurring branch mutation of *Hebe* 'Mrs. Winder'.
Vigor: Moderate.
Growth rate: Approximately 26 cm. per year.
Growth habit: Broad upright.
Plant shape: Rounded.
Suitable container size: 6.0 liter container.
Height: Average 40.0 cm. in height.
Width: Average 50.0 cm. in width.
Hardiness: 0° Centigrade.
Propagation: Terminal cuttings.
Crop Time: 150 days.
Time to initiate roots (summary): Approximately 21 days at 21° C. to produce roots on an initial cutting.

Time to initiate roots (winter): Approximately 28 days at 21° C. to produce roots on an initial cutting.

Time to produce a rooted cutting or liner (summer): Approximately 40 days at 30° C.

Time to produce a rooted cutting or liner (winter): Approximately 55 days at 15° C.

Root system: Fine and fibrous.

Stem:

*Branching habit.*—Freely branching.

*Average number of lateral branches.*—12.

*Pinching.*—Yes.

*Lateral branch diameter.*—1.5 mm. in diameter.

*Lateral branch length.*—8.0 cm. in length.

*Lateral branch strength.*—Strong.

*Stem color.*—187A.

*Pubescence.*—Absent.

*Internode length.*—10 mm. between nodes.

*Shape.*—Round.

*Surface.*—Glabrous.

Foliage:

*Texture.*—Smooth.

*Leaf arrangement.*—Opposite.

*Compound or single.*—Single.

*Quantity of leaves per lateral branch.*—16.

*Leaf shape.*—Oblanceolate.

*Leaf tip.*—Rounded.

*Leaf base.*—Cuneate.

*Leaf margin.*—Entire.

*Leaf length.*—3.0 cm. in length.

*Leaf width.*—1.0 cm. in width.

*Pubescence.*—Absent.

*Young leaf color* (*upper surface*).—187A.

*Young leaf color* (*lower surface*).—187A.

*Mature leaf color* (*upper surface*).—187C.

*Mature leaf color* (*lower surface*).—135C.

*Vein color.*—187C.

*Durability of foliage to stress.*—High.

Flower: Flowering has not been observed.

Disease and pest resistance: Plants of the new *Hebe* have not been observed for disease or pest resistance.

What is claimed is:

1. A new and distinct variety of *Hebe* plant named 'Turkish Delight' as described and illustrated.

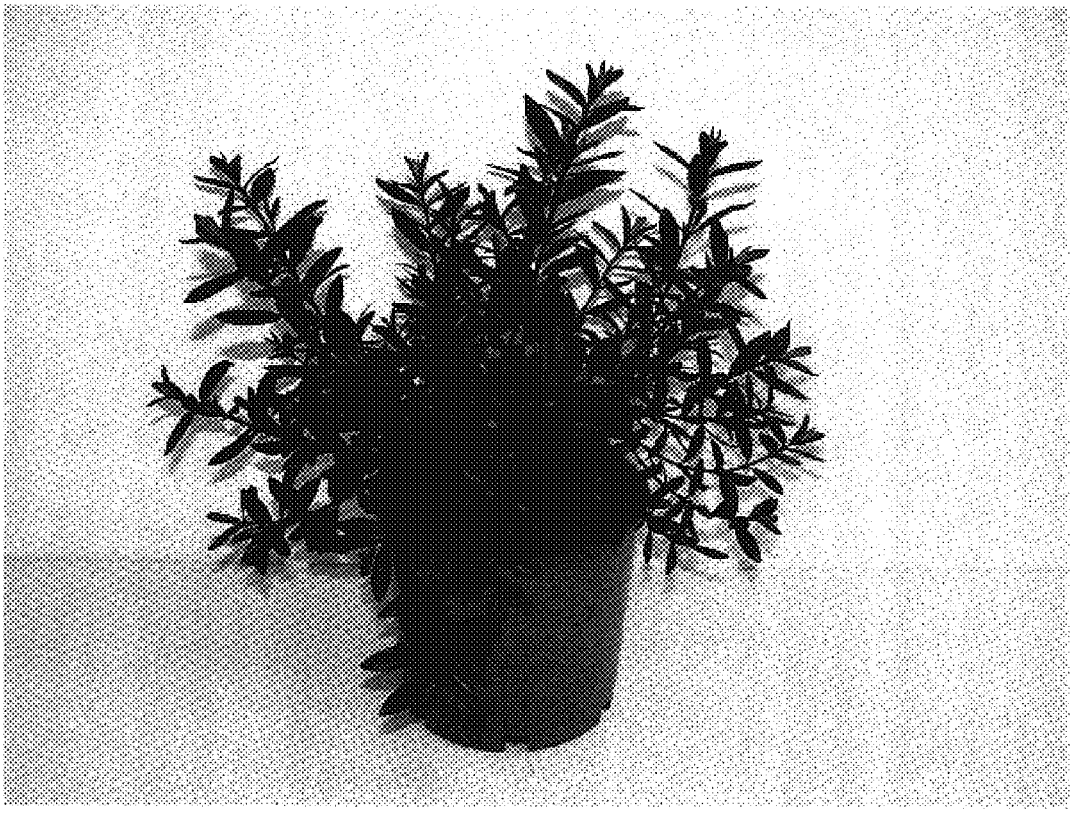

* * * * *